US006337992B1

(12) United States Patent
Gelman

(10) Patent No.: US 6,337,992 B1
(45) Date of Patent: Jan. 8, 2002

(54) PREDICTIVE BOLUS TRACKING

(75) Inventor: Haim Gelman, Migdal-Haemek (IL)

(73) Assignee: Philips Medical Systems Technologies Ltd., Haifa (IL)

( * ) Notice: Subject to any disclaimer, the term of this patent is extended or adjusted under 35 U.S.C. 154(b) by 0 days.

(21) Appl. No.: 09/355,698

(22) PCT Filed: Jan. 29, 1997

(86) PCT No.: PCT/IL97/00036

§ 371 Date: Jul. 29, 1999

§ 102(e) Date: Jul. 29, 1999

(87) PCT Pub. No.: WO98/32376

PCT Pub. Date: Jul. 30, 1998

(51) Int. Cl.[7] .................................................. A61B 5/05
(52) U.S. Cl. ....................... 600/425; 600/431; 600/436; 128/899; 250/336.1; 364/413.15; 364/413.17; 364/413.18; 378/4; 378/21; 378/23; 378/25
(58) Field of Search ......................... 128/899; 600/407, 600/425, 436, 431; 250/336.1; 364/413.15, 413.17, 413.18; 378/25, 10, 19, 17, 4, 8, 16, 98, 98.2, 98.9, 686, 151, 153, 21, 23

(56) References Cited

U.S. PATENT DOCUMENTS

| 5,271,055 A | | 12/1993 | Hsieh et al. |
| 5,301,672 A | * | 4/1994 | Kalender ..................... 128/654 |
| 5,412,562 A | | 5/1995 | Nambu et al. |
| 5,450,464 A | | 9/1995 | Sakakibara |
| 5,459,769 A | | 10/1995 | Brown |
| 5,485,493 A | * | 1/1996 | Heuscher et al. ........... 378/686 |
| 6,167,293 A | * | 12/2000 | Chenevert et al. .......... 600/420 |

FOREIGN PATENT DOCUMENTS

| DE | 195 33 557 A | 11/1996 |
| EP | 0 364 966 A | 4/1990 |
| EP | 0 399 606 A | 11/1990 |

OTHER PUBLICATIONS

"Optimal Contrast Enhancement of the Liver Using Helical (Spiral) CT: Value of SmartPrep"; Silverman et al; American Journal of Radiology, vol. 164 (1995), pp. 1169–1171.

* cited by examiner

Primary Examiner—Marvin M. Lateef
Assistant Examiner—Jeoyuh Lin
(74) Attorney, Agent, or Firm—Fenster & Company Patent Attorneys, Ltd.

(57) ABSTRACT

A method for determining a time for acquiring contrast-enhanced images from a CT scanner of a subject into whom a contrast medium has been injected, the method including:
identifying a region of interest in an initial CT image of the body of a subject;
defining an attenuation data segment corresponding to the region of interest by reprojecting the region of interest in the initial image;
receiving attenuation data within the segment from a subsequent scan of the patient; and
independently processing the attenuation data received within the segment to estimate an optimal time for performing a diagnostic scan of the body, without reconstructing all or a portion of the CT image.

32 Claims, 3 Drawing Sheets

PREDICTIVE BOLUS TRACKING

RELATED APPLICATION

The present application is a US national stage application of PCT/IL97/00036, filed Jan. 29, 1997.

FIELD OF THE INVENTION

The present invention relates generally to CT imaging, and specifically to methods for contrast enhancement in CT imaging.

BACKGROUND OF THE INVENTION

Contrast enhancement in CT imaging, by injection of contrast media into the bloodstream of a subject is well known in the art. A bolus of a suitable contrast medium, for example, comprising iodine, is injected intravenously into the subject's body and is carried by the blood flow to an organ of interest, such as the liver. Features of the organ, such as tumors, which may ordinarily be difficult or impossible to discern, preferentially take up the contrast medium from the blood. After a certain delay, to allow the medium to reach the organ of interest in sufficient concentration, a CT scan of the subject is performed. If the scan is performed at the appropriate time, the contrast-enhanced features of the organ are clearly seen in the resultant CT images.

Generally, in performing such contrast-enhanced CT scans, a standard delay is allowed between the beginning of injection and the beginning of diagnostic scanning, for example 60–70 seconds in liver scans. The time required for the contrast medium to reach sufficient concentration in the organ, however, varies substantially from patient to patient. These variations are the result of differences in cardiac output and other circulatory parameters, and are very difficult to predict. Furthermore, after the concentration has reached its desired value, giving a high contrast for imaging, the medium begins to wash out of the organ, and contrast drops off. Therefore, when a standard scanning delay is used for all patients, a relatively large dose of contrast medium or a relatively long CT scanning period, with consequently increased radiation dosage, must be used in order to ensure that an image of sufficient contrast is captured.

General Electric Medical Systems (Milwaukee, Wis.) has introduced an optional modification to CT scanners of its manufacture known as "SmartPrep," which is intended to provide a patient-dependent variable delay between bolus injection and the beginning of CT scanning. This modification is described in an article by Silverman, et al., entitled "Optimal Contrast Enhancement of the Liver Using Helical (Spiral) CT: Value of SmartPrep," in the American Journal of Radiology, vol. 164 (1995), pages 1169–1171, which is incorporated herein by reference.

In SmartPrep, an initial scan is performed to produce a CT image of a slice through an organ or area of interest the patient's body. A user, generally a physician, marks up to three regions of interest in the image, for example, the aorta, portal vein and hepatic parenchyma, if the liver is the object of the procedure. Injection of the contrast medium is begun, and starting a short time thereafter, a sequence of CT scans are performed of the same slice, preferably at a reduced level of irradiation. Images from these scans are reconstructed, and the CT values, in Hounsfield units (H), in the images for each of the regions of interest are compared with baseline values from the initial scan. When the CT value in one of the regions, preferably the aorta, reaches a desired threshold over the corresponding baseline, the sequence of scans is terminated. After a delay of approximately 10 sec. a diagnostic helical scan over the organ or area is initiated.

SmartPrep thus allows the beginning of the diagnostic scan to be cued according to the time it takes the contrast medium to reach an area in the image slice in sufficient concentration to produce strong image contrast. According to the above-mentioned article, SmartPrep is effective in optimizing the delay from the bolus injection to the beginning of diagnostic scanning, such that, for example, in a sample of 75 patients studied by Silverman and co-workers, delay times ranged from 57 to 86 sec, as against the standard 60–70 sec delay. These delays are typical for contrast-enhanced imaging of the hepatic parenchyma, which normally receives the contrast medium through the portal vein with a lag of a number of seconds relative to the aorta.

SmartPrep may not be effective, however, for imaging features and areas of organs that receive the contrast medium with only a short lag behind the appearance of the medium in the aorta, before there has been a substantial amount of perfusion through the body. Such features include arterial lesions in the liver and pulmonary areas. The delays inherent in reconstructing the images from the sequence of CT scans, and then waiting until the threshold is reached before terminating this sequence, are typically greater than the short time that it takes the contrast medium to reach the organ.

SUMMARY OF THE INVENTION

It is an object of the present invention to provide an improved method for contrast-enhanced CT scanning, by predicting when a bolus of contrast medium will reach a desired concentration level in an area of suspected pathology in the body.

In preferred embodiments of the present invention, a patient is positioned in a CT scanner, and X-ray attenuation data are acquired with respect to a slice through an area of suspected pathology in the patient's body. The data are preprocessed, filtered and back-projected, as is known in the art, to reconstruct a reference CT image of the slice. One or more regions of interest (ROIs) are identified within this slice, wherein preferably, one of the ROIs includes the aorta or other major artery feeding a site of the suspected pathology, and another ROI includes the site itself. These ROIs are reprojected onto the preprocessed attenuation data, so as to define segments within the data corresponding respectively to each of the ROIs.

A bolus of a contrast medium, for example, comprising iodine, is injected into the patient's bloodstream, and a CT scan of the slice, preferably a continuous dynamic scan, is initiated. During this scan, attenuation data from the ROI-related segments are acquired and preprocessed continuously. Preferably, the preprocessed attenuation data are tracked so as to generate one or more functional curves describing the increase in attenuation over time, due to influx of the contrast medium into the ROIs. The shapes of the initial portions of these curves are used to predict when the attenuation at the site of the suspected pathology will reach a predetermined value or peak. Based on this prediction, the continuous dynamic scan is terminated, and a helical scan is initiated, preferably automatically, to acquire a diagnostic, contrast-enhanced image of the area.

Preferably, the segments defined within the preprocessed attenuation data comprise segments of data acquired with respect to each ROI from a plurality of different angular views. As the CT scanner scans through these different views in succession, the preprocessed attenuation data acquired in each view are used in turn in generating the functional curves. Preferably, the data acquired in different views are combined, for example, by correlation, to increase the sensitivity of detection of increases in attenuation.

Alternatively or additionally, the attenuation data from the ROI-related segments may be back-projected to reconstruct images of one or more of the ROIs, as described in a PCT patent application filed on even date with the present application and entitled "REAL TIME DYNAMIC IMAGE CONSTRUCTION" and which is assigned to the assignee of the present patent application, and whose disclosure is incorporated herein by reference. The CT values in the ROIs may be used to generate the functional curves, which are used in controlling the scanner as described herein.

Preferably, the one or more functional curves are displayed by the scanner, for example, on a video screen, as they are generated. This display allows a user to view, substantially in real time, the progress of the contrast medium entering the subject's body. If the user observes that the curves do not show a normal increase in attenuation, he or she may intervene, for example, to initiate the diagnostic scan independent of the prediction or to terminate the scan, as appropriate.

CT images of the slice may be reconstructed intermittently while the attenuation tracking is going on. However, unlike methods of bolus tracking known in the art, such as the above-mentioned SmartPrep method, the present invention enables the progress of the bolus to be predicted without reconstructing the full slice image. The progress of the bolus may be predicted using only the preprocessed attenuation data, independent of and without the need for any image reconstruction, or by reconstructing only the ROI portion of the CT image. Therefore, the present invention allows much more rapid and precise prediction of the time at which the attenuation at the site of the suspected pathology will reach a desired value. Typically, in preferred embodiments of the present invention, the prediction is completed within a few seconds, for example seconds, so that the diagnostic scan can begin when the bolus reaches the region of interest, for example about 10 seconds after the attenuation at the aorta begins to rise. Therefore, unlike methods known in the art, the present invention may also be used in diagnostic scanning of arterial phase lesions. The rapid prediction afforded by the present invention may also be useful in reducing the dosages of contrast medium and radiation that are administered to the subject.

Although preferred embodiments are described herein with reference to certain combinations of axial and helical scans by the CT scanner, it will be appreciated that the principles of the present invention, whereby the attenuation data themselves are used directly and rapidly in predicting changes in contrast within an area of suspected pathology, may be applied using other scanning combinations and procedures.

The present invention will be more fully understood from the following detailed description of the preferred embodiments thereof, taken together with the drawings in which:

DETAILED DESCRIPTION OF PREFERRED EMBODIMENTS

Figure 1:
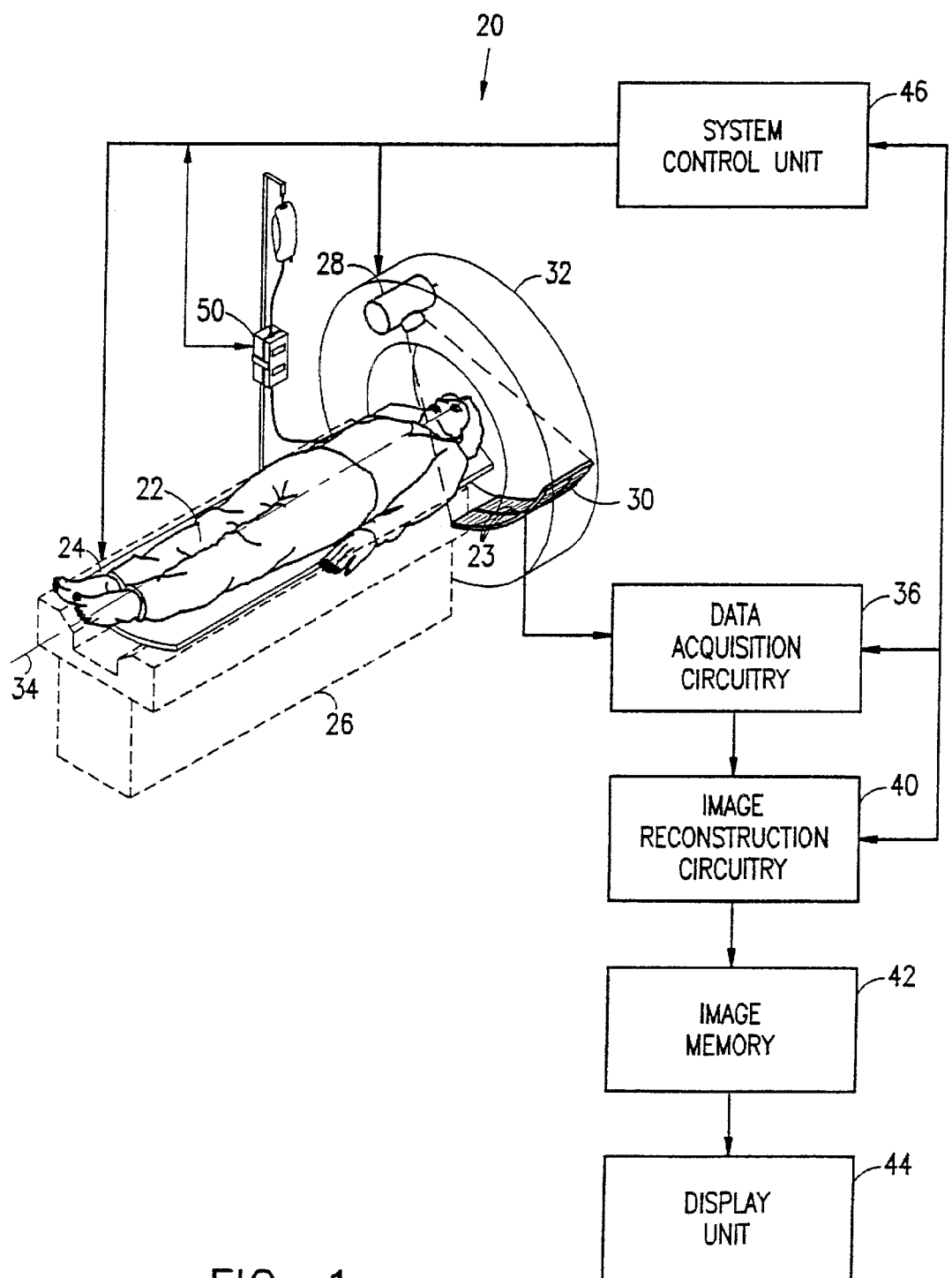
FIG. 1 is a schematic illustration of a CT scanner, operative in accordance with a preferred embodiment of the present invention.

Reference is now made to FIG. 1, which shows a CT scanner 20, operative in accordance with a preferred embodiment of the present invention. Scanner 20 comprises a bed 24, supported by a base 26, on which bed a subject 22 lies while his body is being imaged by the scanner. Scanner 20 further comprises an X-ray tube 28, which irradiates subject 22, and a detector array 30, which receives X-rays from tube 28 and generates signals responsive to the attenuation of the X-rays in passing through the subject's body.

Tube 28 and array 30 are mounted on an annular gantry 32, so as to revolve about subject 22. Bed 24 is advanced through gantry 32 along an axis 34, which is generally parallel to the long axis of the subject's body. As will be described below, in preferred embodiments of the present invention, scanner 20 operates alternately in an axial mode, wherein bed 24 is held stationary while tube 28 and array 30 revolve thereabout, or in a helical mode, wherein tube 28 and array 30 revolve simultaneously with the advance of bed 24 through gantry 32.

Scanner 20 as pictured in FIG. 1 is of a type known in the art as a third-generation CT-scanner, characterized in that both tube 28 and detector array 30 revolve about subject 22. It will be appreciated, however, that the principles of the present invention and the methods of image reconstruction to be described below are equally applicable to other types of CT scanners, in particular fourth-generation CT scanners, in which the detectors form a substantially stationary ring around subject 22.

At each of a plurality of selected locations of tube 28 along its scan path, data acquisition circuitry 36 acquires a "view," i.e., the circuitry receives signals from each element 23 of array 30 responsive to X-ray attenuation. For each view, circuitry 36 performs signal normalization and logarithm operations, as are known in the art, to derive X-ray attenuation data corresponding to each of elements 23. Image reconstruction circuitry 40 received these data and interpolates, filters and back-projects the data, using methods known in the art, to produce one or more planar image slices through the body of subject 22. A plurality of these planar image slices may be used to reconstruct a three-dimensional CT image set of all or a portion of the body of subject 22. Preferably, these image slices are stored in image memory 42 and displayed by display unit 44, and they may be otherwise printed and/or processed as is known in the art. Preferably a system controller 46 controls and coordinates the operation of the various elements of scanner 20.

An infusion pump 50, for example, a power syringe pump, as is known in the art, is charged with a predetermined quantity of a contrast medium, for example, iodine, and is connected intravenously to subject 22. Preferably, pump 50 is coupled to controller 46 so that scanning operation of scanner 20 can be triggered by the activation of the pump, as will be described below.

Figure 2:
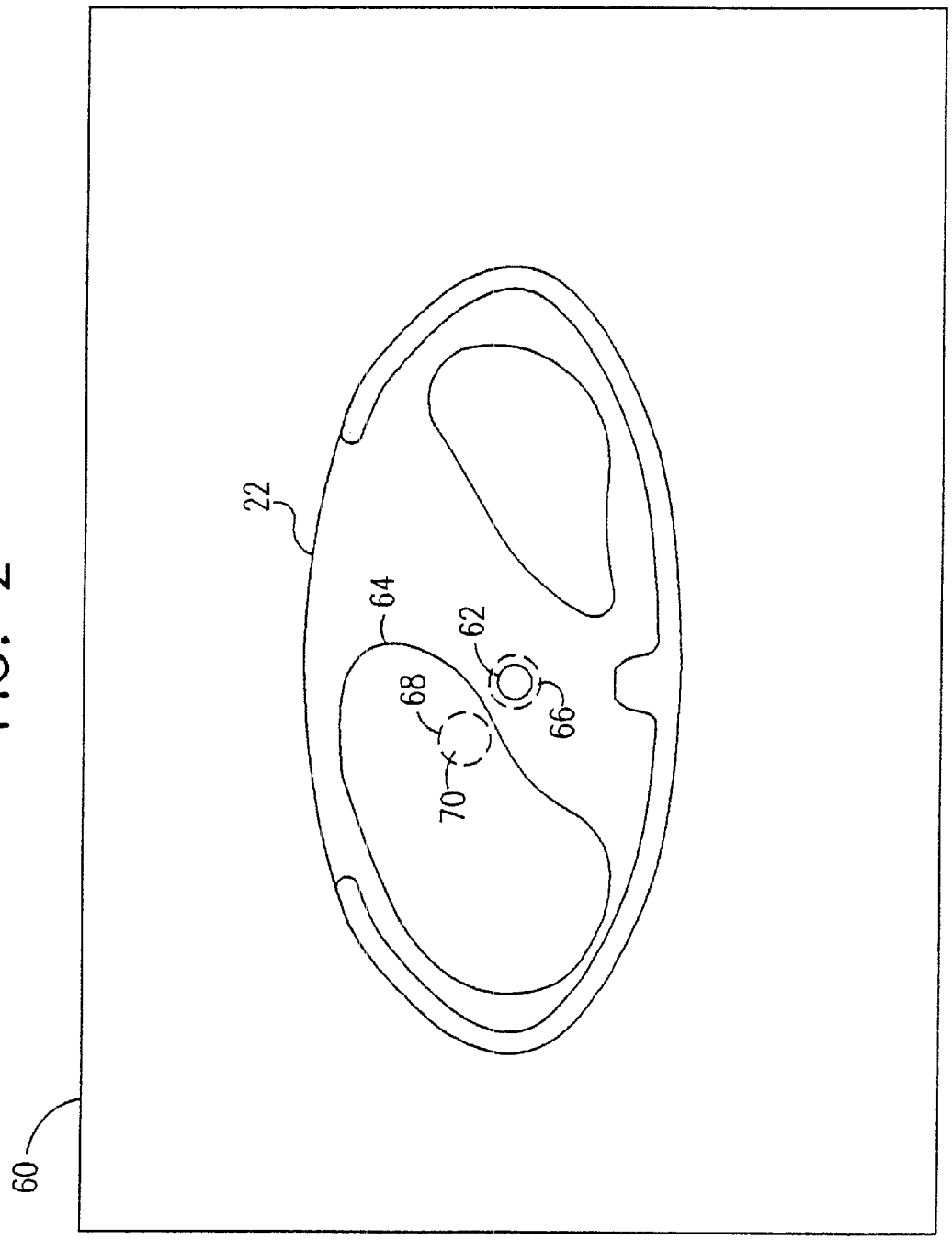
FIG. 2 is a schematic illustration showing an image reconstructed by the CT scanner of FIG. 1, on which regions of interest have been marked, in accordance with a preferred embodiment of the present invention.

FIG. 2 is a schematic representation of a sectional image 60, acquired by scanner 20, of a "slice" through the body of subject 22, in accordance with a preferred embodiment of the present invention. Image 60 is acquired, preferably by means of a single axial scan of scanner 20 at a selected position of bed 24, before initiating operation of pump 50. The position of the bed is chosen so that the slice intersects an area of suspected pathology, in this case liver 64.

A user of scanner 20 observes image 60 on display 44, and indicates regions of interest (ROIs) in the image: preferably, a first ROI 66 at the location of aorta 62, and a second ROI 68 at a site of suspected lesion 70. Additional ROIs may be indicated at other locations, for example, along a blood vessel leading to site 70. Although ROIs 66 and 68 are round, other shapes, such as rectangular ROIs, may similarly be used. The locations of the ROIs are input to scanner 20 and are preferably displayed on image 60, for example, using dashed lines as shown in FIG. 2.

The locations and extents of ROIs 66 and 68 are fed back to image reconstruction circuitry 40, which reprojects these image areas back onto the preprocessed attenuation data received from data acquisition circuitry 36. The object of this reprojection is to define segments within the attenuation data that correspond, respectively, to each of the ROIs. Each such segment comprises attenuation data acquired along rays from tube 28 to array 30 that pass through the corresponding ROI. Preferably, the segments that are defined with respect to each ROI include attenuation data acquired from multiple views at different angles of revolution of gantry 32 with respect to subject 22.

Figure 3:
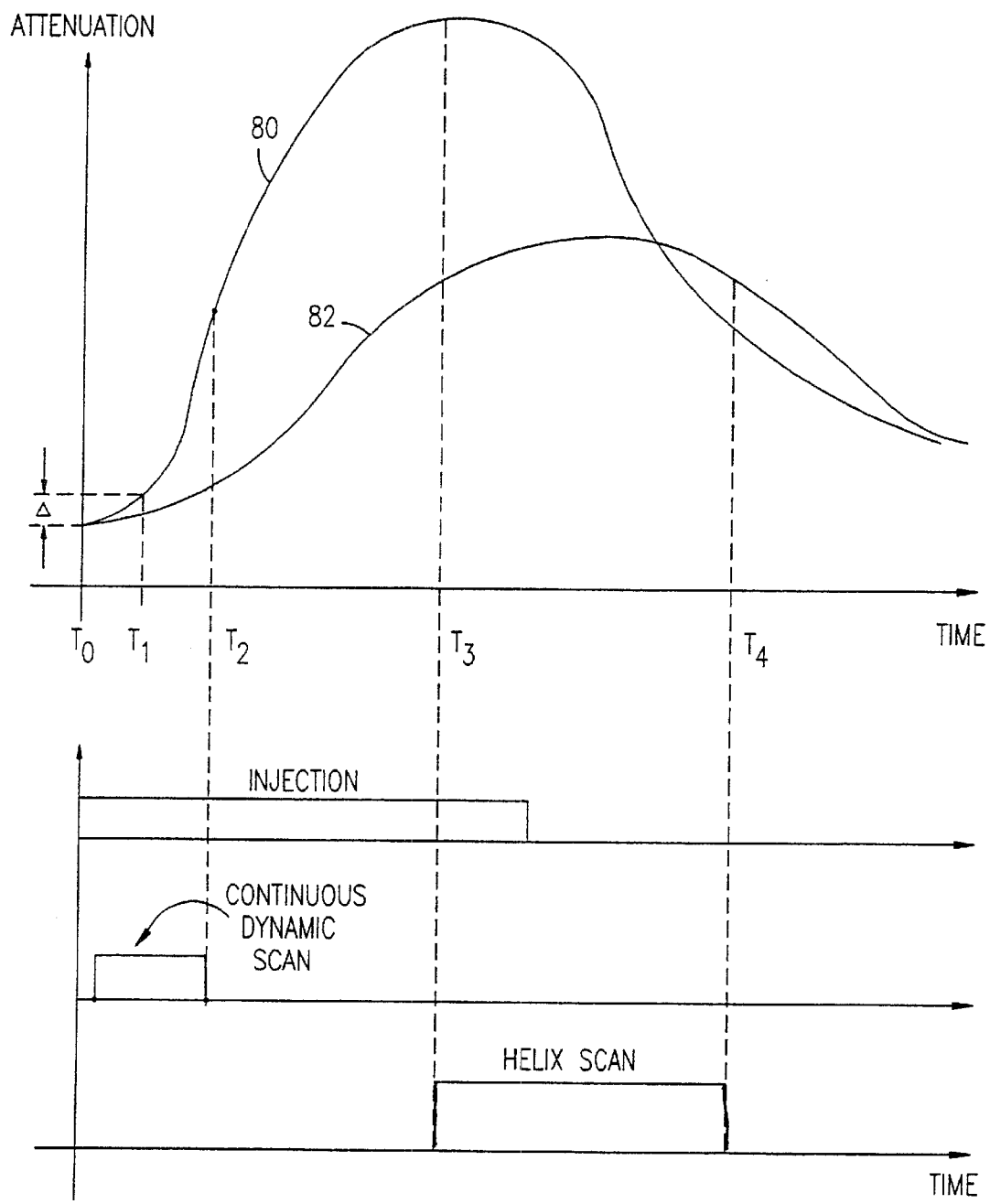
FIG. 3 is a graph that schematically illustrates an aspect of the operation of the scanner of FIG. 1, in accordance with a preferred embodiment of the present invention.

FIG. 3 is a graph that schematically illustrates the operation of scanner 20, after initial image 60 has been acquired and ROIs 66 and 68 have been chosen, in accordance with a preferred embodiment of the present invention. The upper portion of the figure includes curves 80 and 82, respectively representing measured attenuation in the segments corresponding to ROIs 66 and 68, as a function of time. The attenuation is measured directly on the reprojected segments of preprocessed attenuation data, without back-projecting the data to find CT values. The lower portion of the figure is a timing diagram, on the same time scale as the upper portion.

At a beginning time $T_0$, pump 50 is activated to begin injecting the contrast medium into subject 22. Shortly thereafter, controller 46 initiates a continuous dynamic axial scan of scanner 20 at the position of bed 24 at which image 60 was acquired. In this continuous dynamic scan, tube 28 revolves continuously around subject 22, and attenuation data are acquired and preprocessed. Image reconstruction circuitry 40 optionally back-projects the data to reconstruct and intermittently update an image of the slice, like image 60. However, curves 80 and 82 are generated without reference to such an image. Preferably, during the continuous dynamic scan, tube 28 is controlled to operate at a low level of irradiation of subject 22, in order to reduce the radiation dosage that the subject receives.

As shown by curves 80 and 82 in FIG. 3, the attenuation data in the data segments corresponding respectively to ROIs 66 and 58 are tracked by controller 46, or by another suitable computing device, independently of any image reconstruction going on. Preferably, as gantry 32 scans through its multiple angular views, the preprocessed attenuation data acquired within the data segments corresponding to the ROIs in the different views are used in turn in generating the curves. Preferably, the data acquired in different views are combined, for example, by correlation, to increase the sensitivity of detection of increases in attenuation.

Alternatively or additionally, the attenuation data from the ROI-related segments may be back-projected to reconstruct images of one or more of ROIs 66 and 68, as described in the above-mentioned PCT patent application. The CT values in the ROIs may then be used to generate curves 80 and 82, which are used in controlling the scanner as described herein.

However, the curves are generated, they are, preferably, also plotted graphically on display 44.

Beginning at a time $T_1$, when a curve 80 rises by an increment $\Delta$ over its baseline, $T_0$ value, the attenuation data in curve 80 are fitted to a model function, for example, a second order polynomial. This attenuation tracking and fitting continue as long as required to obtain an accurate curve fit, terminating at a time $T_2$. The fit is used to predict when curve 80 will reach its peak, i.e., when the contrast medium in aorta 62 will reach its maximum concentration. Preferably, curve 82 is monitored simultaneously with curve 80, to predict how much longer the medium will take to reach its maximum concentration at site 70 in liver 64.

Once the fitting and prediction computations have been completed, at time $T_2$, the continuous dynamic scan of scanner 20 is automatically brought to an immediate "soft stop." The scanner is then positioned and prepared to begin a diagnostic helix scan. The helix scan begins at a time $T_3$, when curve 82 is predicted to be nearing its maximum. Shortly after time $T_3$, the injection of the contrast medium by pump 50 is terminated, and the scan continues until a time $T_4$, when the curve has begun to drop off.

Time $T_3$ may be as little as 10–15 seconds from the initial of injection at time $T_0$, particularly in the case of lesions that receive the contrast medium in the arterial phase of blood flow in liver 64, i.e., receiving the contrast medium directly from the arteries. The rapid acquisition and fitting of the attenuation data, without the need for image reconstruction, in accordance with the principles of the present invention, enable this prompt operation. Alternatively, time $T_3$ may be in the range of 50–90 seconds after $T_0$ for portal venous-phase lesions, as in other bolus tracking methods, as are known in the art, such as the above-mentioned SmartPrep method. In either case, the early, accurate determination of times $T_3$ and $T_4$ in accordance with the method of the present invention allows optimal diagnostic images to be acquired by scanner 20, with minimal dosages of contrast medium and radiation to subject 22.

The user of scanner 20, observing curves 80 and 82 on display 44, may intervene in the event that the curves do not follow a normal, expected pattern. For example, if subject 22 has poor blood circulation, the curves may rise abnormally slowly. In this case, the user may preferably override the automatic operation of the scanner to begin the helical scan at a default or estimated delay time. Alternatively, a malfunction in the operation or intravenous connection of pump 50 will also be observed to affect the rise of the curves, in which case the scan is preferably terminated while the problem is corrected.

Although the above preferred embodiment has been described with reference to lesions of liver 64, it will be appreciated that the principles of the present invention may equally be applied to contrast-enhanced scanning of other organs of the body, as is known in the art. Furthermore, although in the above preferred embodiment, a helical-mode diagnostic scan in used to acquire contrast-enhanced images, the method described here may be used, mutatis mutandis, together with axial-mode contrast-enhanced CT scanning techniques.

It will also be appreciated that the preferred embodiments described above are cited by way of example, and the full scope of the invention is limited only by the claims.

What is claimed is:

1. A method for determining a time for acquiring contrast-enhanced images from a CT scanner of a subject into whom a contrast medium has been injected, the method comprising:

identifying a region of interest in an initial CT image of the body of a subject;

defining an attenuation data segment corresponding to a region of interest by reprojecting the region of interest in the initial image;

receiving attenuation data within the segment from a subsequent scan of the patient; and independently processing the attenuation data received within the segment to estimate an optimal time for performing a diagnostic scan of the body, without reconstructing all or a portion of the CT image.

2. A method according to claim 1 and including receiving an indication of the time of injection of a bolus of contrast medium.

3. A method according to claim 1 and including, performing a diagnostic scan at the estimated optimal time.

4. A method according to claim 3, wherein performing the diagnostic scan comprises performing a helical scan.

5. A method according to claim 1, wherein defining the attenuation data segment comprises defining segments in multiple angular views, and wherein processing the attenuation data comprises combining the data from the multiple views to determine the optimal time for performing the diagnostic scan.

6. A method according to claim 1, wherein processing the attenuation data comprises predicting a future value of the attenuation within the segment, and using the predicted value to estimate the optimal time for performing the diagnostic scan.

7. A method for determining a time for acquiring contrast-enhanced images corresponding to a region of interest from a body of a subject into whom a contrast medium is injected, from a CT scanner, the method comprising:

receiving attenuation data within a segment from a scan of the subject using the scanner;

predicting a future value of the attenuation within the segment, based on the attenuation data received; and estimating an optimal time for performing a diagnostic scan of the body, using the predicted value.

8. A method according to claim 7 and including receiving an indication of a time of injection of a bolus of contrast medium.

9. A method according to claim 7 and including performing a diagnostic scan of the subject at the estimated time.

10. A method according to claim 9, wherein performing the diagnostic scan comprises performing a helical scan.

11. A method according to claim 7, and comprising identifying the region of interest in an initial CT image of the body, wherein defining the attenuation data segment comprises reprojecting an initial image to define the segment.

12. A method according to claim 7, wherein predicting the future value of the attenuation comprises fitting the attenuation data received within the segment to a functional curve.

13. A method according to claim 7, wherein predicting the future value of the attenuation comprises predicting a time at which the attenuation will reach a desired value thereof.

14. A method according to claim 13, wherein estimating the optimal time for performing the scan comprises determining a scan period which includes the time at which the attenuation will reach the maximum value.

15. A method according to claim 7, wherein defining the attenuation data segment comprises defining two attenuation data segments, and wherein predicting the future value of the attenuation comprises determining a delay between an attenuation increase in a first one of the two segments and a corresponding attenuation increase in the second of the segments.

16. A method according to claim 1, wherein receiving the attenuation data comprises receiving attenuation data from a continuous dynamic scan of the body.

17. A method according to claim 7 wherein receiving the attenuation data comprises receiving the attenuation data from a continuous dynamic scan of the body.

18. A CT scanner including:

a scanning system capable of receiving attenuation data, constructing a CT image in response thereto and defining a region of interest on said image;

a signal interface capable of receiving signals representative of a time of injection of a bolus of contrast material and of producing a signal indicating when a diagnostic scan should be performed;

bolus time arrival apparatus, that defines an attenuation data segment corresponding to a region of interest by reproducing data in the region of interest in an initial image and including a processor that independently processes attenuation data received within the segment in subsequent scans to estimate an optimal time for performing a diagnostic scan of the body.

19. A scanner according to claim 18, wherein the bolus time arrival apparatus defines attenuation segments in multiple angular views, and the processor combines the data from the multiple views to estimate the optimal time for performing the diagnostic scan.

20. A scanner according to claim 18, wherein the processor predicting a future value of the attenuation within the segment, and uses the predicted value to determine the optimal time for performing the diagnostic scan.

21. A CT scanner including:

a scanning system capable of receiving attenuation data, constructing a CT image in response thereto; and bolus time arrival apparatus, that receives attenuation data from a plurality sequential scans and which estimates an optimum future time for performing a diagnostic scan based on the sequential attenuation data, said estimated future time being estimated prior to said future time.

22. A scanner according to claim 21 wherein the scanning system is capable of identifying a region of interest in an initial CT image of the body, wherein the bolus time arrival apparatus defines attenuation data segment on which said bolus time arrival apparatus bases its estimate by utilizing attenuation data only in segments based on reprojection of the region of interest.

23. A scanner according to claim 21, wherein the bolus time arrival apparatus fits a function of the attenuation data to a functional curve.

24. A scanner according to claim 21 wherein bolus time arrival apparatus is capable of defining the estimated future time as a time at which the attenuation will reach a desired value thereof.

25. A scanner according to claim 21, wherein the scanner performs scans for a period starting said estimated future time and during a scan period which includes the time at which the attenuation will reach the maximum value.

26. A scanner according to claim 21 wherein the sequential attenuation data is received from a continuous dynamic scan of the body.

27. A scanner according to claim 26 wherein the scan is a helical scan.

28. A method for determining a time for acquiring contrast-enhanced images from a body of a subject into whom a contrast medium is injected, from a CT scanner, the method comprising:

receiving attenuation data from a scan of the subject using the scanner; and estimating an optimal time for performing a diagnostic scan of the body, using the received attenuation data;

wherein estimating an optimal time includes:
predicting a future value of the attenuation, based on the attenuation data received; and
estimating the optimal time based on the predicted future value of attenuation.

29. A CT scanner including:

means for acquiring an initial CT image of the patient;

means for defining a region of interest in the initial CT image;

means for defining an attenuation data segment corresponding to the region of interest by reprojecting the region of interest in the initial image;

means for injecting a bolus of contrast medium into a patient;

means for performing subsequent scans of the patient after said injection;

means for receiving attenuation data within the segment from the subsequent scans;

means for independently processing the attenuation data received within the segment to determine an optimal time for performing a diagnostic scan of the body; and means for performing a diagnostic scan of the patient responsive to the determination of the optimal time to acquire a contrast enhanced CT image.

30. CT imaging apparatus including means for determining the time of an optimal scan after injection of a contrast medium, comprising:

a CT scanner;

means for acquiring an initial CT image of the patient;

means for identifying a region of interest in the initial CT image;

means for receiving an indication of the time of injection of a bolus of contrast medium;

means for defining an attenuation data segment corresponding to the region of interest by reprojecting the region of interest in the initial image;

means for performing subsequent scans of the patient;

means for receiving attenuation data within the segment from the subsequent scans;

means for independently processing the attenuation data received within the segment to determine an optimal time for performing a diagnostic scan of the body; and means for performing a diagnostic scan of the patient responsive to the determination of the optimal time to acquire a contrast enhanced CT image.

31. CT imaging apparatus, comprising:

means for performing a scan of a patient;

means for receiving attenuation data within a segment of the scan;

means for predicting a future value of attenuation within the segment, based on the attenuation data received;

means for determining an optimal time for performing a diagnostic scan of the body, using the predicted value; and means for performing a diagnostic scan of the patient at the determined time.

32. A method for determining a time for acquiring contrast-enhanced images from a body of a subject into whom a contrast medium is injected, from a CT scanner, the method comprising:

receiving attenuation data from a scan of the subject using the scanner;

reconstructing an image of a portion of the subject from the attenuation data;

receiving additional attenuation data from a scan of the subject using the scanner; and estimating an optimal time for performing a diagnostic scan of the body, using the received additional attenuation data, without reconstructing all or a portion of an image of the subject, responsive to the received additional data.

* * * * *